(12) United States Patent
Lehrman et al.

(10) Patent No.: US 8,740,805 B2
(45) Date of Patent: Jun. 3, 2014

(54) SYSTEM AND METHOD FOR ANTICIPATING THE ONSET OF AN OBSTRUCTIVE SLEEP APNEA EVENT

(75) Inventors: Michael L. Lehrman, Washington, DC (US); Shun-Yong Zinn, North Potomac, MD (US); Michael D. Halleck, Frederick, CO (US)

(73) Assignee: Sleep Methods, Inc., Bethesda, MD (US)

(*) Notice: Subject to any disclaimer, the term of this patent is extended or adjusted under 35 U.S.C. 154(b) by 509 days.

(21) Appl. No.: 12/881,989

(22) Filed: Sep. 14, 2010

(65) Prior Publication Data

US 2011/0066059 A1    Mar. 17, 2011

Related U.S. Application Data

(60) Provisional application No. 61/276,597, filed on Sep. 14, 2009.

(51) Int. Cl.
*A61B 5/08*    (2006.01)

(52) U.S. Cl.
USPC .................. 600/529; 600/484; 600/538

(58) Field of Classification Search
CPC ..... A61B 5/4806; A61B 5/4818; A61B 7/003
USPC .......................... 600/529–543, 484
See application file for complete search history.

(56) References Cited

U.S. PATENT DOCUMENTS

| 6,261,238 | B1* | 7/2001 | Gavriely | 600/532 |
|---|---|---|---|---|
| 6,375,623 | B1* | 4/2002 | Gavriely | 600/534 |
| 6,666,830 | B1 | 12/2003 | Lehrman et al. | |
| 7,542,536 | B2 | 6/2009 | Barnette et al. | |
| 2004/0225226 | A1* | 11/2004 | Lehrman et al. | 600/529 |
| 2004/0254467 | A1* | 12/2004 | Jackson | 600/450 |
| 2006/0145878 | A1* | 7/2006 | Lehrman et al. | 340/575 |
| 2008/0082018 | A1* | 4/2008 | Sackner et al. | 600/538 |
| 2008/0243014 | A1* | 10/2008 | Moussavi et al. | 600/529 |

OTHER PUBLICATIONS

Cavusoglu et al, An efficient method for snore/nonsore classification of sleep sounds, Jul. 6, 2007, IOP Publishing, Physiol. Meas. 28 (2007) pp. 841-853.*

U.R. Abeyratne, et al., "Pitch-Jitter Analysis of Snoring Sounds for the Diagnosis of Sleep Apnea", Proc. 23rd Annual EMBS Int. Conf., retrieved from the internet on Dec. 8, 2010, p. 2072-2075.*

Chandan K. Karmakar, et al., "Power spectral analysis of ECG signals during obstructive sleep apnoea hypopnoea epochs", 2007 IEEE, p. 573-576.*

U.R. Abeyratne, et al., "Pitch-Jitter Analysis of Snoring Sounds for the Diagnosis of Sleep Apnea", Proc. 23rd Annual EMBS Int. Conf., retrieved from the internet on Dec. 8, 2010, p. 2072-2075.

(Continued)

*Primary Examiner* — Jacqueline Cheng
*Assistant Examiner* — Puya Agahi

(57) ABSTRACT

Systems and methods for detecting a general breathing event and for anticipating an onset of an obstructive sleep apnea (OSA) event. The method for detecting a general breathing event includes receiving a plurality of signals from at least one microphone. The method also includes determining a one-sided power spectral density from the received signals. The method further includes distinguishing each received signal as either a breath signal or a background noise signal. The method still further includes calculating a breath signature by processing each breath signal.

20 Claims, 9 Drawing Sheets

(56) References Cited

OTHER PUBLICATIONS

A. Travaglini, et al., "Respiratory Signal Derived from Eight-lead ECG", Computers in Cardiology 1998, vol. 25, p. 65-68.

Notification of Transmittal of the International Search Report and the Written Opinion of the International Searching Authority, or the Declaration dated Dec. 20, 2010 in connection with International Patent Application No. PCT/US2010/048794.

* cited by examiner

| Name | Sex | Age | Number of qualified intervals of silence | Corresponding sleep study duration | Index |
|---|---|---|---|---|---|
| SMI3 | Male | 49 | 144 | 3.0 | 48.7 |
| SMI4 | Male | 77 | 121 | 4.8 | 25.4 |
| SMI5 | Male | 59 | 43 | 2.7 | 15.9 |
| SMI6 | Male | 43 | 40 | 1.6 | 25.6 |
| SMI7 | Male | 34 | 120 | 2.7 | 44.2 |
| SMI8 | Male |  | 88 | 3.4 | 26.0 |
| SMI9 | Male | 77 | 235 | 3.3 | 71.4 |

FIG. 1

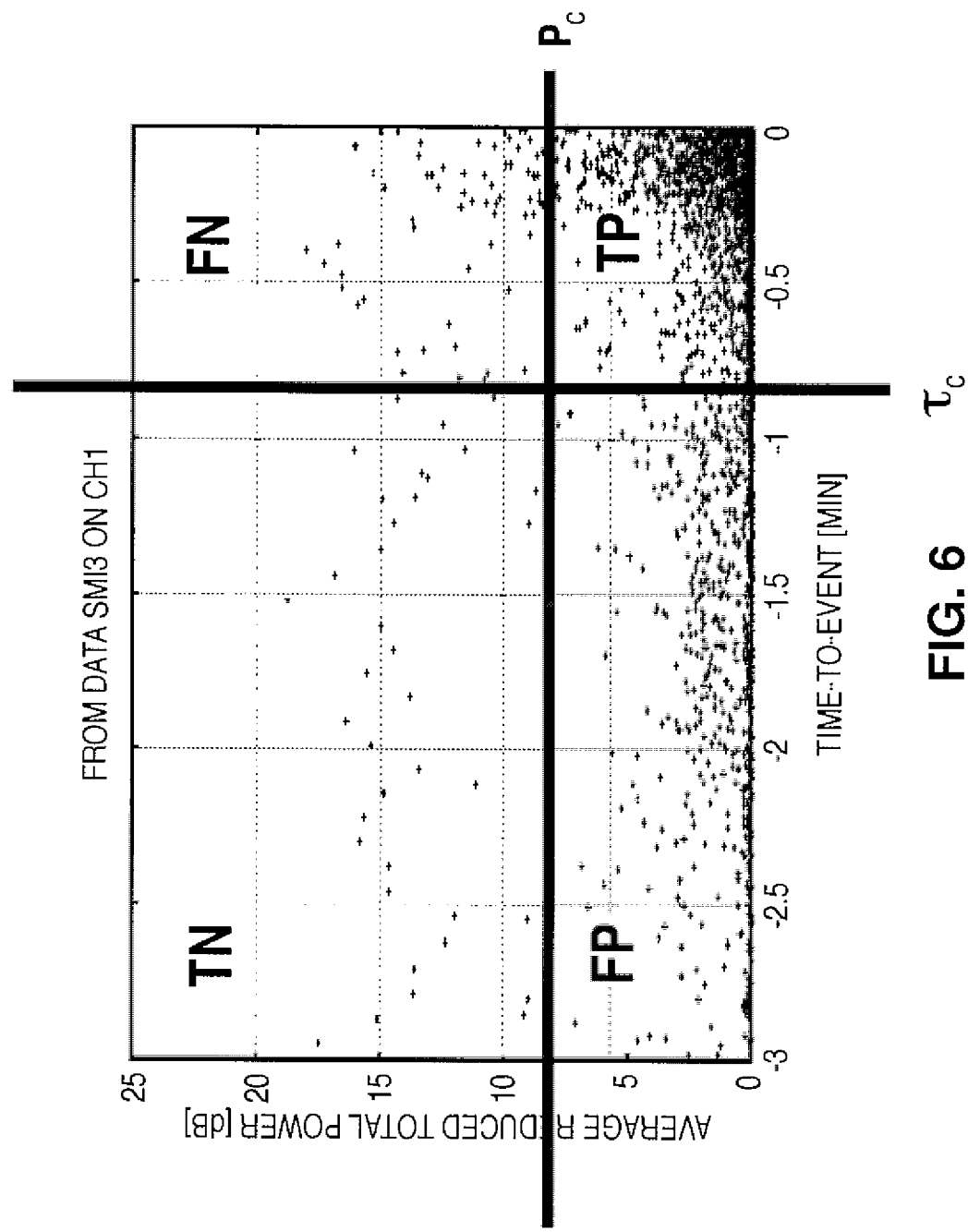

SYSTEM AND METHOD FOR ANTICIPATING THE ONSET OF AN OBSTRUCTIVE SLEEP APNEA EVENT

CROSS-REFERENCE TO RELATED APPLICATION(S) AND CLAIM OF PRIORITY

The present application is related to U.S. Provisional Patent Application No. 61/276,597, filed Sep. 14, 2009, entitled "SYSTEM AND METHOD FOR DETECTING THE ONSET OF AN OBSTRUCTIVE SLEEP APNEA EVENT". Provisional Patent Application No. 61/276,597 is assigned to the assignee of the present application and is hereby incorporated by reference into the present application as if fully set forth herein. The present application hereby claims priority under 35 U.S.C. §119(e) to U.S. Provisional Patent Application No. 61/276,597.

TECHNICAL FIELD

This disclosure is generally directed to sleep apnea and more particularly to systems and methods for anticipating the onset of an obstructive sleep apnea event.

BACKGROUND

Apnea is the cessation of breathing (at least 80% reduction in air flow), marked by a drop in blood oxygen saturation of at least 3%, arousal often associated with gasping, and an adrenergic response (initiated by a survival reflex in which epinephrine/adrenaline gets dumped into the blood stream increasing blood pressure and heart rate). Sleep apnea is the cessation of breathing during sleep. Sleep apnea is a common sleep disorder that affects over twelve million (12,000,000) people in the United States. Persons with sleep apnea may stop and start breathing several times an hour while sleeping. Each individual episode of the cessation of breathing is referred to as a sleep apnea event.

Two other sleep disorders related to apnea are hypopnea (characterized by incomplete narrowing of the airway resulting in a flow of 50 to 80% of baseline, drop in blood oxygen saturation of 3%, sometimes arousal, and sometimes an adrenergic response which always leads to arousal) and RERA, (Respiratory Effort Related Arousal, characterized by increasing respiratory effort leading to arousal but without the blood chemistry changes seen in apnea/hypopnea).

When a person stops breathing during sleep the person's brain soon senses that oxygen levels in the blood are low and carbon dioxide levels in the blood are high. The brain then sends emergency signals to the body to cause the body to try to increase gas exchange in the lungs to increase the amount of oxygen and to decrease the amount of carbon dioxide. The body's autonomic physiological reflexes initiate survival reactions such as gasping for air, the production of enzymes to constrict arteries to increase blood pressure, and the production of enzymes to increase heart rate. The person will then usually gasp for air and thereby restore the effective gas exchange of oxygen and carbon dioxide in the lungs. This causes the sleep apnea event to end.

The brain may also cause the body's autonomic physiological reflexes to release large amounts of adrenaline in order to stir the person to gasp for air. Over a period of time repeated rushes of adrenaline in the body can have negative effects and can lead to heart damage and other medical problems.

Often the person wakes up while gasping for air. Even if the person does not become conscious while gasping for air, the body's sleep state is interrupted and the body is physiologically stressed during each sleep apnea event. Sleep apnea events can occur multiple times during a period of sleep. That is, the process of ceasing to breathe, becoming physiologically stressed, and gasping for air may be repeated numerous times during a period of sleep. Successive sleep apnea events cause a person to experience many short interrupted periods of sleep.

Interrupted periods of sleep can produce varying levels of fatigue, lack of energy, and daytime sleepiness. Other symptoms may include restless sleep, loud and sometimes heavy snoring, morning headaches, irritability, mood changes, behavior changes, and similar emotional or physical disorders. While mild forms of sleep apnea may exist without apparent harm to the individual, severe cases may lead to such conditions as weight gain, impotency, high blood pressure, stroke, mental problems, memory loss, and even death.

There are two forms of sleep apnea. The two forms are central sleep apnea and obstructive sleep apnea. At the present time, central sleep apnea and obstructive sleep apnea are thought to originate from two different sources. Central sleep apnea appears to be linked to a malfunction of the brain that interferes with neurological signals that normally control the breathing process. Obstructive sleep apnea is caused by a blockage of the breathing airway that completely stops the flow of air to and from the lungs. A common form of obstructive sleep apnea occurs when fleshy tissue in a sleeping person's throat collapses and seals off the pharyngeal airway. A condition called mixed sleep apnea results when central sleep apnea events and obstructive sleep apnea events alternate.

Successful treatment for obstructive sleep apnea must ensure that a person's breathing passages remain open during sleep. The simplest treatments include weight reduction, change in body position while sleeping, avoidance of alcohol, avoidance of sedatives, and similar changes in lifestyle. When anatomical obstructions are found to be the source of obstructive sleep apnea, surgery may be required for removal of enlarged tonsils, enlarged adenoids, excess tissue at the back of the throat, and similar types of obstructions. In more extreme cases, an opening may be created in the trachea in order to bypass the obstruction that is blocking the airway during sleep.

One device for the treatment of obstructive sleep apnea is a device that pumps positively pressurized air into a mask worn over the nose. This device provides what is known as nasal continuous positive airway pressure (CPAP). When the mask and air flow are properly adjusted, the air pressure opens the upper air passage enough to prevent snoring and obstructive sleep apnea. The disadvantages of the CPAP treatment include 1) discomfort and sleep disruption caused by the nose mask and the mechanism for connecting the mask to the air pumping device, 2) original and on-going cost for the apparatus, and 3) inconvenience when the sleeping location changes.

Therefore, there is a need in the art for an improved system and method for treating obstructive sleep apnea.

SUMMARY

A system and method for detecting a general breathing event are provided. The method includes receiving a plurality of signals from at least one microphone. The method also includes determining a one-sided power spectral density from the received signals. The method further includes distinguishing each received signal as one of: a signal associated with a breath and a signal associated with a background noise. The method still further includes calculating a breath signature by processing each signal associated with a breath.

A system and method for anticipating an onset of an obstructive sleep apnea (OSA) event are provided. The method includes receiving signals associated with a plurality of breaths. The method also includes calculating an average reduced total power of each of the breaths. The method further includes determining a linear least-square-fit of a power curve associated with the average reduced total power of the breaths. The method still further includes, based on the average reduced total power and the linear least-square-fit, categorizing each breath as one of: a positive breath (a breath in which no OSA event is predicted) and a negative breath (a breath which may be soon followed by an OSA event).

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of this disclosure and its features, reference is now made to the following description, taken in conjunction with the accompanying drawings, in which:

FIG. 6 depicts a graph illustrating threshold lines separating positive and negative data points, and false and true data points, according to one embodiment of the present disclosure.

DETAILED DESCRIPTION

The present disclosure provides a system and method for anticipating the onset of an obstructive sleep apnea event. Prior art systems and methods are directed toward detecting and treating an obstructive sleep apnea event after the obstructive sleep apnea event has occurred. The system and method described herein is able to anticipate and terminate the onset of an obstructive sleep apnea event before the obstructive sleep apnea event fully develops. That is, the onset of an obstructive sleep apnea event can be predicted or anticipated before the sleeping person actually stops breathing. This allows steps to be taken to prevent the obstructive sleep apnea event from occurring.

Figures 1, 2A:
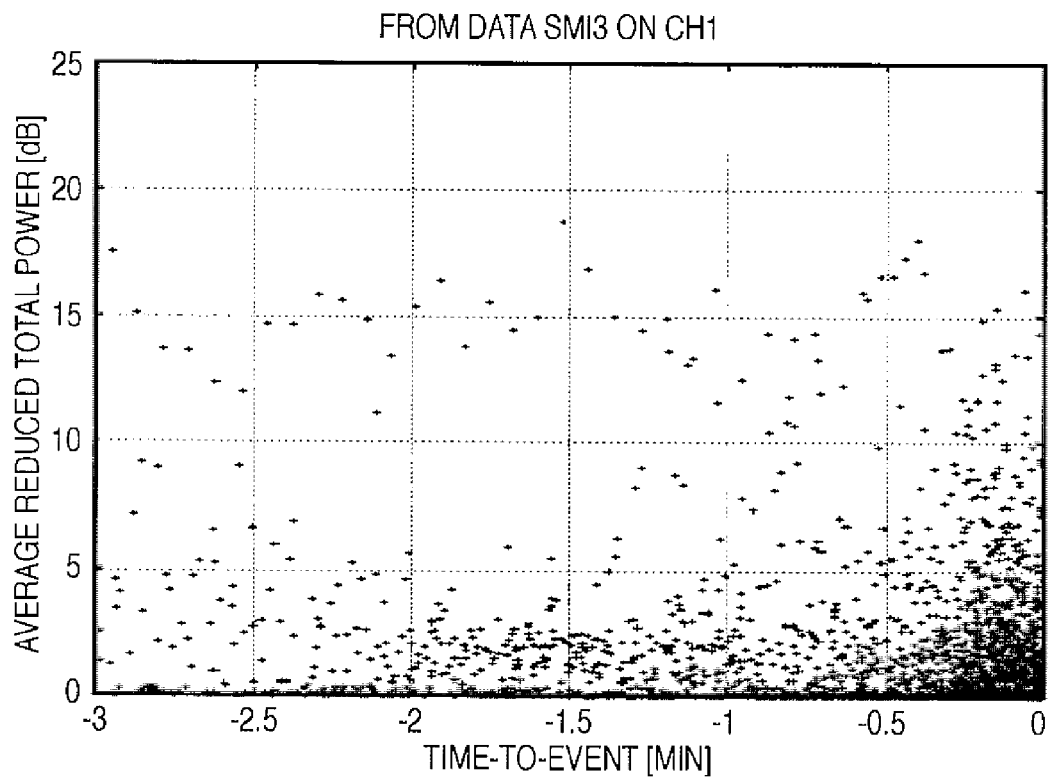
FIG. 1 depicts a list of patient information for patients involved in a sleep study.
FIG. 2A depicts a scatter plot and a histogram for one patient in the sleep apnea detection study, according to one embodiment of the present disclosure.
Figures 2, 2A:
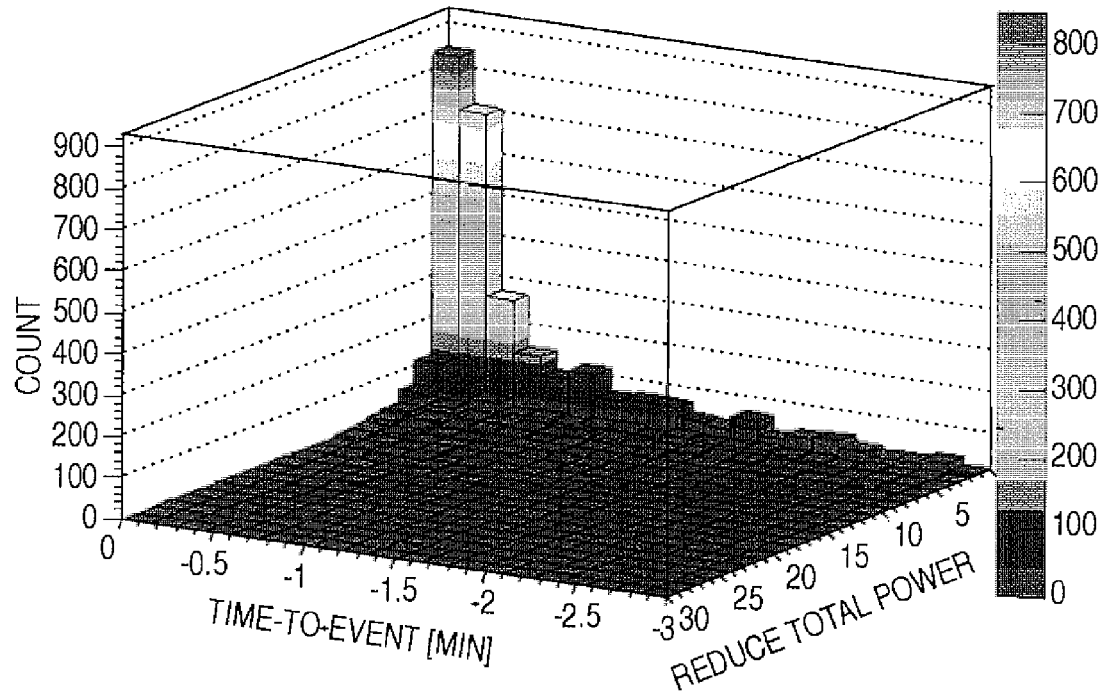

In order to develop the system and method disclosed herein, a study was performed on a number of patients. In the study, microphones where placed around each patient's neck, and sounds received by the microphones were recorded while the patient slept. FIG. 1 lists the code name, sex, age, and other associated properties, including the number of intervals of silence that are ten seconds or longer, for certain patients in the study.

FIG. 2A depicts a scatter plot and a histogram for one patient in the sleep apnea detection study, according to one embodiment of the present disclosure. The scatter plot and histogram are produced using all breath data points collected during an overnight sleep study of the patient.

The scatter plot depicts breath power of the patient in dB versus the time-to-event in minutes. The y-axis in the scatter plot is "AVERAGE REDUCED TOTAL POWER [dB]." The average reduced total power, a scalar quantity associated with each breath, is calculated to be near zero when a person is not breathing and to be noticeably greater when a person is breathing, so that a data analyzer, such as a computer program, can easily tell whether the person is breathing or not at any given moment. A method for calculating the average reduced total power is described herein in detail.

Analysis performed in the study shows that a breath can be detected by examining signals in a frequency range of approximately 200 Hz to 800 Hz. The sound data recorded by the set of microphones placed around each patient's neck are processed for noise removal and for minimizing spectral leakage that degrades the quality of frequency-domain data. The pre-processed data in a time domain are converted to a power spectrum by using a Fast Fourier Transform technique (described in greater detail below). After subtracting noise in the power spectrum, the power spectrum is integrated over the frequency range of interest (i.e., 200-800 Hz) and then divided by the frequency range to yield the average reduced total power. Thus, when a person is not breathing, the background noise contained in the sound data is subtracted off to yield a zero value for the average reduced total power. However, when a person is breathing, the breath signal in the frequency range is averaged, which yields a nonzero value for the average reduced total power.

The x-axis in the scatter plot is "TIME-TO-EVENT [Minutes]." The time-to-event of a breath is calculated by subtracting the start time of the nearest apnea event occurring after the breath from the time of that breath, so that the time-to-event is always negative. Every breath of a sleep study is associated with the time-to-event and average reduced total power.

The 3D histogram has x-, y-, and z-axes that are labelled as "TIME-TO-EVENT", "REDUCED TOTAL POWER", and "COUNT", respectively. Note that the 3D histogram plot is presented with the time-to-event axis running in the opposite direction (compared with that of the scatter plot) to reveal the details near the origin.

The count, found on the z-axis of the histogram, is the number of data points found in the given histogram bin. When a breath data point is added to the histogram, its bin location is calculated from the time-to-event and average reduced total power. The count of the corresponding bin is increased by one for a data point. By examining the distribution of the count over the histogram range near zero time-to-event, one can identify the signature of the onset of apnea events. In our analysis, the onset signature is the high count of data points at low reduced total power, i.e., weakening of breath.

Figures 1, 2B:
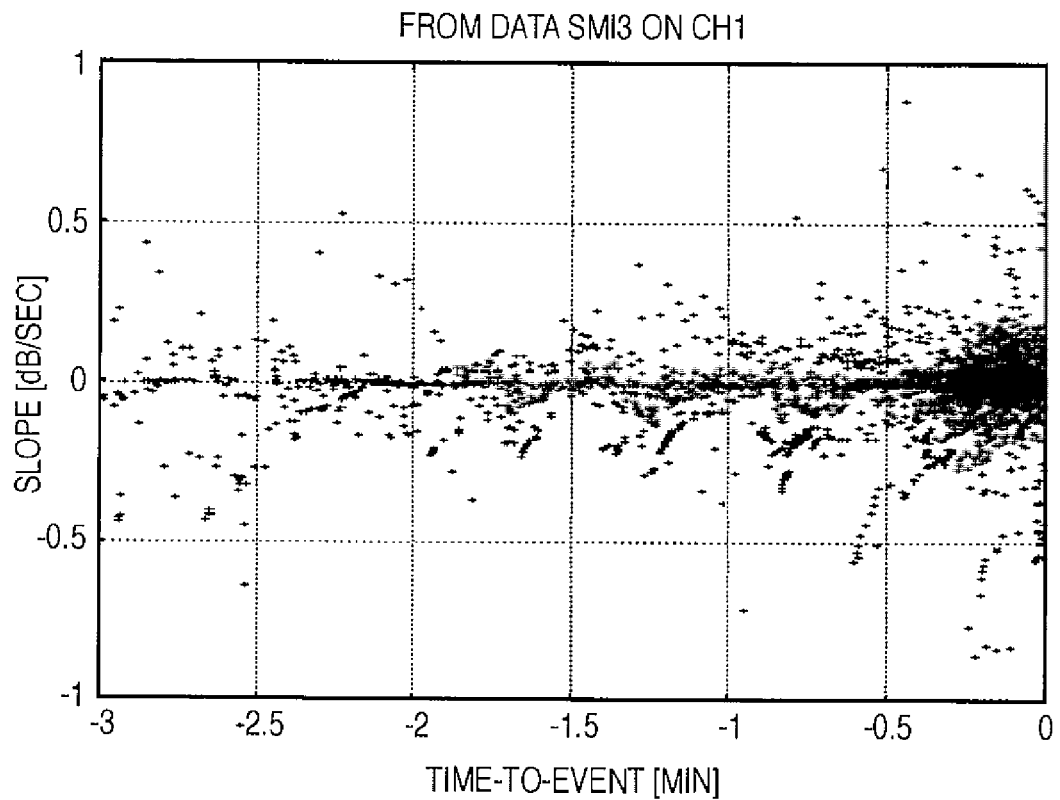
FIG. 2B depicts a second scatter plot and histogram for one patient in the sleep apnea detection study, according to one embodiment of the present disclosure.
Figures 2, 2B:
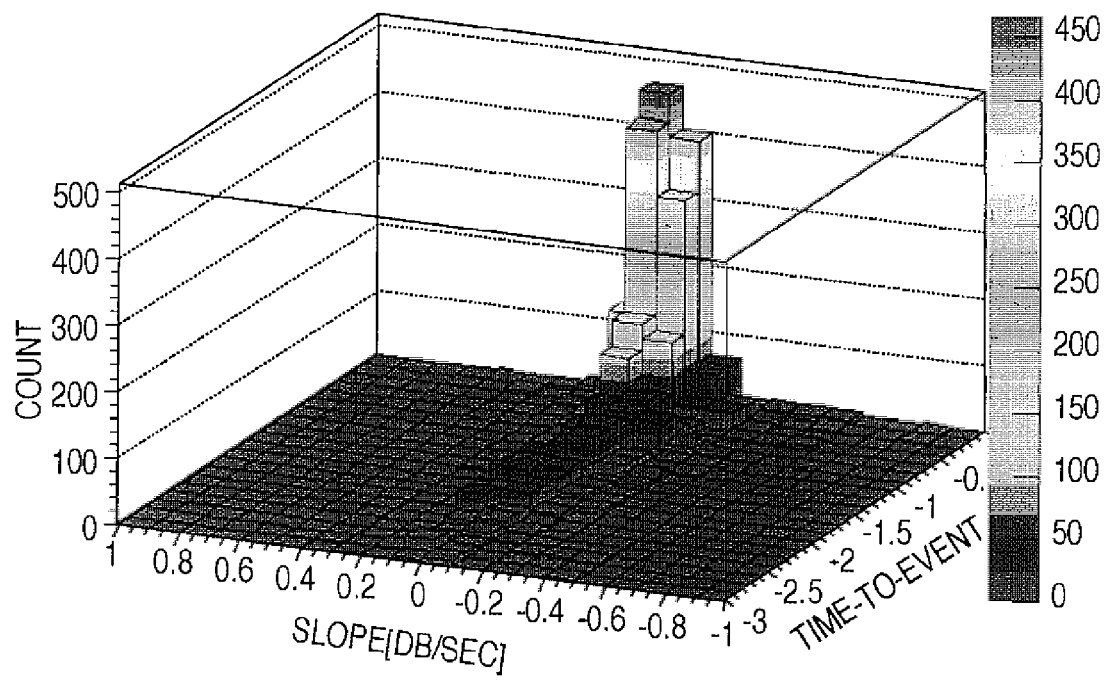

FIG. 2B depicts a second scatter plot and histogram for one patient in the sleep apnea detection study, according to one embodiment of the present disclosure. The scatter plot and histogram are based on the same data points as those in FIG. 2A. However, the scatter plot and histogram of FIG. 2B include measurement of a slope on one axis, instead of average reduced total power. The slope at a given time-to-event is taken from a linear fit of the breath data points shown in the scatter plot of FIG. 2A that occur over a rolling time interval (e.g., twenty seconds, which corresponds to approximately five breaths). A negative slope implies the breath powers are decreasing over time. A positive slope implies the breath powers are increasing over time.

In order to facilitate anticipation of obstructive apnea events, it may be helpful to first detect general events, which are defined as something other than noise. Some examples of a general event are a conversation, a breath, a cough, etc. In order to perform data analysis that will detect a general event, the pre-processed data shown in a time domain in FIG. 2A is converted to a power spectrum using Fast Fourier Transform techniques. A forward Fourier Transform to convert a continuous signal h(t) from a time domain to a frequency domain is:

$$H(f) \equiv \int_{-\infty}^{+\infty} h(t) \exp(2\pi i f t) dt$$

Since the signal data from the microphones are sampled into discrete data points, a discrete Fourier Transform technique is used. First, discrete signal sampling occurs:

$$h_k = h(t_k), t_k = k\Delta$$

where k={0, 1, 2, ..., N−1}, N is the number of samples taken during the sampling interval (e.g., 256 samples), and Δ is the sampling interval in seconds. Then, a forward Fourier Transform technique computes $H_n$ at $f_n = n/N\Delta$ where n={−N/2, ..., N/2}. (Note that the frequency spacing is inversely proportional to the sampling interval for a fixed number of samples, i.e., $f_n - f_{n-1} = 1/N\Delta$.) It is noted that $H_n$ is related to $H(f_n)$ via:

$$H(f_n) \approx \Delta \cdot H_n$$

Next, a power spectrum P(f), called a "one-sided power spectral density", is determined:

$$P(f) = |H(f)|^2 + |H(-f)|^2$$

The forward Fourier Transform of one or more Gaussian functions can be calculated analytically, yielding an exact closed-form formula. One or more Gaussian functions may be used to verify the forward Fourier Transform technique.

Figure 3:
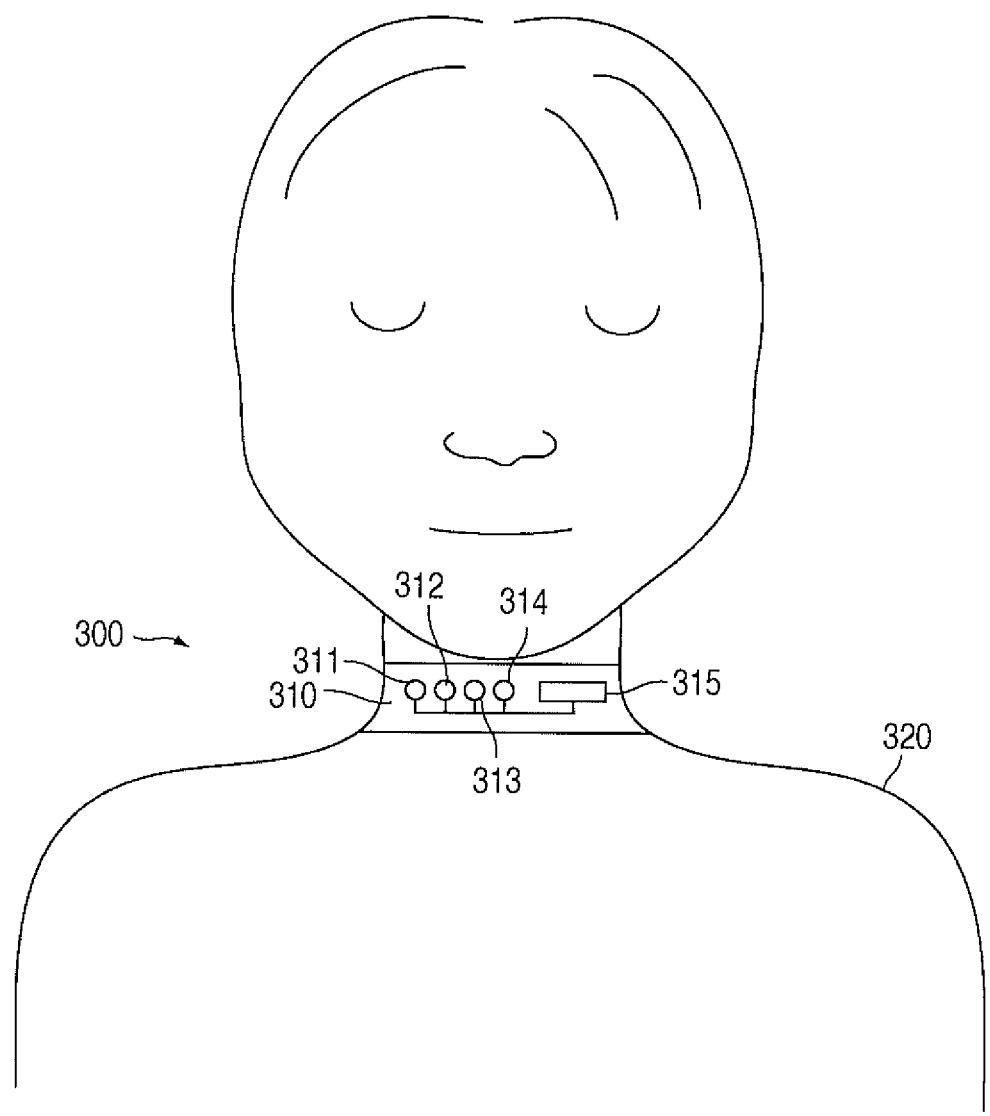
FIG. 3 depicts a device for anticipating the onset of an obstructive sleep apnea (OSA) event, according to one embodiment of the present disclosure.

FIG. 3 depicts a device for anticipating the onset of an obstructive sleep apnea (OSA) event, according to one embodiment of the present disclosure.

Device 300 includes a soft, pliant collar 310 that is worn around the neck of a patient 320. The collar 310 includes microphones 311-314 and a microcontroller 315. In certain embodiments, the microcontroller 315 may include a battery or other power supply configured to power the microcontroller 315 and the microphones 311-314. In other embodiments, the battery or other power supply may be external to the microcontroller 315 and/or the collar 310.

When one or more of the microphones 311-314 detect acoustic changes associated with the advent of an apneic or hypopneic event or other physiological condition, the one or more microphones 311-314 transmit signals associated with the acoustic changes to the microcontroller 315. The microcontroller 315 then processes the signals as described below in order to predict the onset of the OSA event.

Although FIG. 3 depicts one embodiment of a device for anticipating the onset of an OSA event, other embodiments are within the scope of this disclosure. For example, although collar 310 is depicted with four microphones 311-314, it will be understood that more or fewer microphones may be used. As another example, microcontroller 315 may include other hardware, software, or firmware configured to process acoustic signals. More specifically, microcontroller 315 may include one or more processors and one or more memories configured to store data related to the acoustic signals. One or more of these elements may be external to collar 310.

Figure 4A:
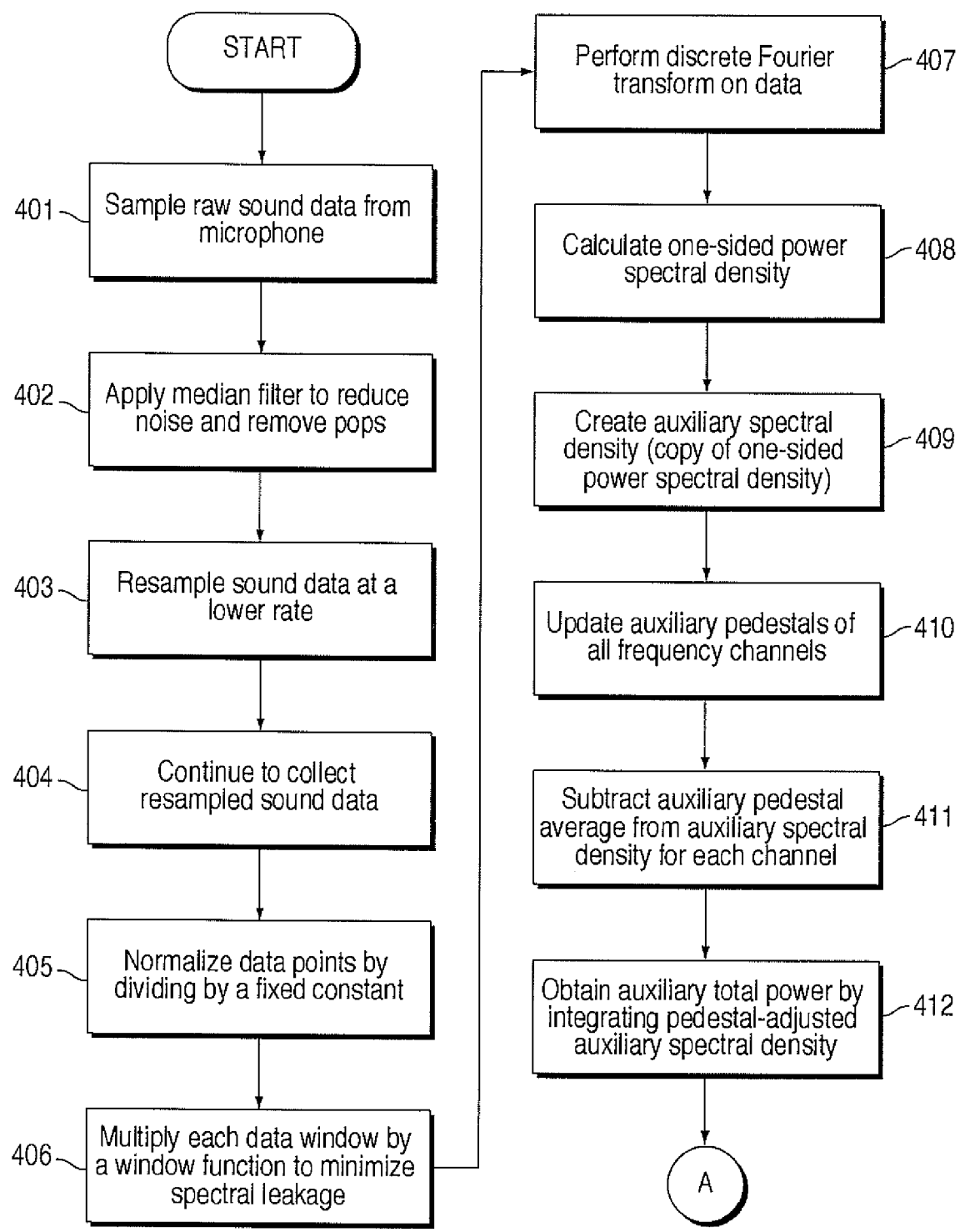
FIGS. 4A, 4B, and 4C depict a method for detecting general events, according to one embodiment of the present disclosure.
Figure 4B:
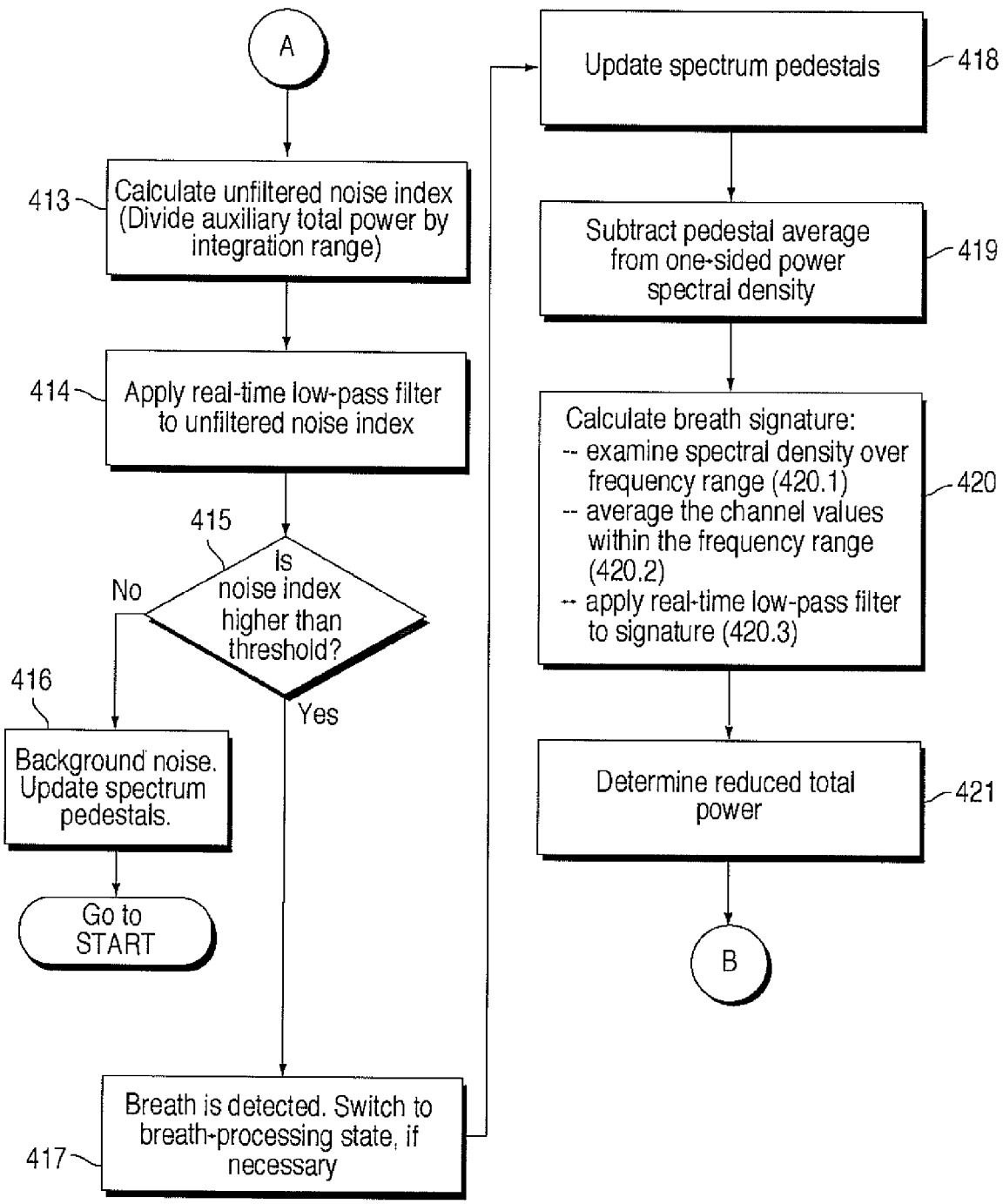
Figure 4C:
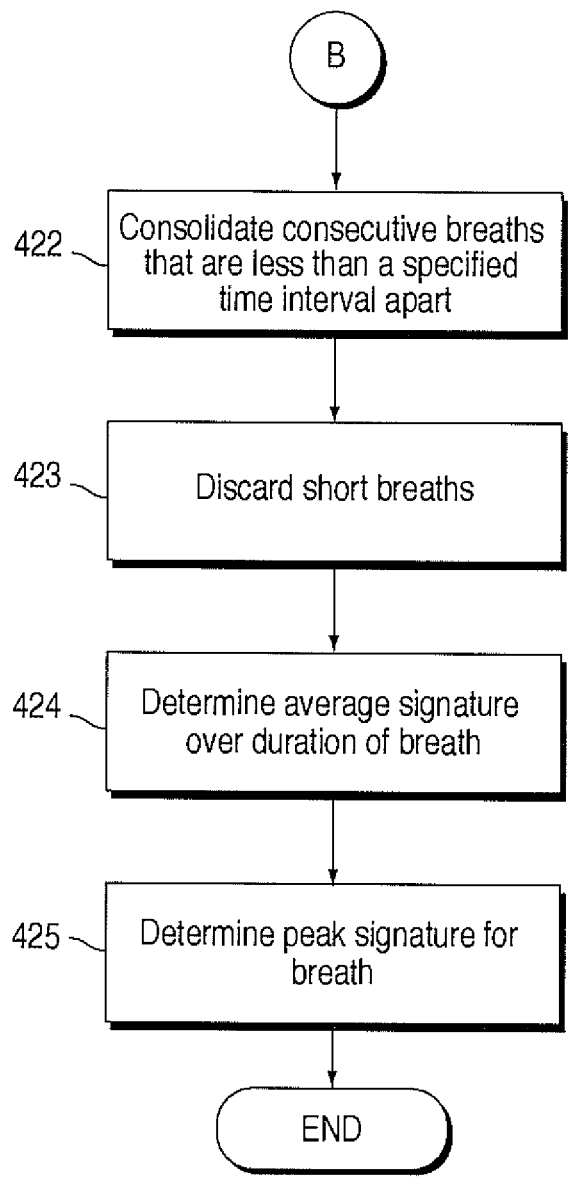

FIGS. 4A, 4B, and 4C depict a method for detecting general events, according to one embodiment of the present disclosure. Because the signal level of normal breaths is near the noise floor, the separation of general event signals from the noise is not an easy task. However, the following method enables distinguishing the general event signals from noise. In certain embodiments, the method may be implemented as an algorithm or computer program in a data processing system.

The initial steps of the disclosed method relate to data sampling and noise reduction. First, raw sound data from one or more microphones (e.g., microphones 311-314) located on or near a sleeping person is sampled (step 401). Because the detection of apnea events must occur quickly to be helpful, the raw sound data is "live" (i.e., concurrent with the present moment) or reflects a very short delay. In one advantageous embodiment, the raw data is sampled at a rate of 96,000 Hz.

Next, in order to reduce the noise and to remove pops, a median filter is applied (step 402). In one advantageous embodiment, the median filter has a magnitude of 7 points.

Next, the raw data is resampled at a lower rate (step 403). As noted earlier, the frequency spacing is inversely proportional to the sampling interval. With a lower sampling rate (and thereby longer sampling interval), the frequency spacing gets smaller. This implies more Fourier transformed data points available in the frequency range of our interests. Thus resampling at a lower rate results in a more detailed frequency spectrum of the sound data.

In one advantageous embodiment, the raw data is resampled at a rate of 4800 Hz. To improve the quality of resampling, a Lanczos filter is employed. In certain embodiments, the Lanczos filter has a radius equal to 1.5 times the sample window. Thus, in certain advantageous embodiments, the down-sampling ratio (e.g., 96,000 Hz to 4800 Hz, or 20:1) with the Lanczos filter results in a 61-point filter (2× the 1.5 radius×the 20:1 ratio+the 1 midpoint). In certain embodiments, the use of the resampling filter can be very important in isolating breath signals from the noise. In other embodiments, data may be sampled only at the lower rate, thus obviating the need for sampling at the higher rate.

The next few steps relate to computation of a one-sided power spectral density. As time passes, the resampled data continues to be collected to form a data window (step 404). In certain embodiments, the data window consists of 256 data points. Consecutive data windows in the time domain overlap substantially. For example, in one advantageous embodiment, the consecutive windows overlap 84%. The overlapping helps to make the change in the frequency spectrum smooth enough for detection of a signal rising up from the background.

Next, the data points are normalized by dividing them by a fixed constant to make them fall in a range numerically reasonable for analysis (step 405). For example, in certain embodiments, the data acquisition system may 24 bits in width. By setting the normalization constant to 65,536, all values will fall within the range of [−256, 256].

Next, each data window is multiplied by a window function to minimize the spectral leakage (step 406). In certain embodiments, the window function may be a Kaiser window having a value alpha=6.0. Next, a discrete Fourier transform is performed (step 407). In certain embodiments, the discrete Fourier transform is performed using 256 bins in accordance with the number of data points in the data window.

Next, a one-sided power spectral density is calculated in dB using the formula $$10*\log(P/P_0)$$

where P is the sum of powers at given positive and negative frequencies (step 408). It is noted that $P_0$ is unity numerically but includes physical units. If the power is zero before taking the logarithm, the corresponding value in dB would be negative infinity, which would destroy the pedestal estimate. This may be prevented by enforcing a minimum power value. In certain embodiments, based on an average of twenty channels and a normalization factor equal to 65,536, a practical minimum for the power is found to be −94.50 dB. If the power of a channel is smaller than the minimum, the minimum value is assigned.

The next few steps relate to distinguishing a signal from background noise. In step 409, a copy is made of the one-sided power spectral density. The copy may be referred to as the "auxiliary spectral density."

Next, the auxiliary pedestals of all frequency channels are updated (step 410). The auxiliary pedestals represent the noise floor when there is no signal. This step is performed by keeping track of a number of points (e.g., 128 points) per channel for trending the average and standard deviation, then adding a new data point, then updating the average and standard deviation. In certain embodiments, a new point is always accepted (i.e., no outliers are rejected).

Next, the auxiliary pedestal average is subtracted from the auxiliary spectral density for each channel (step 411). This produces a pedestal-adjusted auxiliary spectral density.

Next, the auxiliary total power is obtained by integrating the pedestal-adjusted auxiliary spectral density (step 412).

Next, the auxiliary total power is divided by the integration range (e.g., 2400 Hz) (step 413). The resulting value may be referred to as the "unfiltered noise index."

Next, a real-time low-pass filter is applied to the unfiltered noise index (step 414). In certain embodiments, the low-pass filter has a cut-off frequency of 0.375 Hz. The filter output may be referred to as the "filtered noise index" or simply the "noise index."

Next, the value of the noise index is considered (step 415). If the noise index is lower than a threshold, (e.g., 0.0 dB), it is considered to be in the background. For background noise, the spectrum pedestals are updated as detailed below (step 416), and then the algorithm starts over to detect a breath. If it rises above the threshold and remains so for a period of time, a breath is considered to have occurred.

The spectrum pedestals are updated as follows (step 416). Similar to step 410, this step is performed by keeping track of a number of points (e.g., 128 points) per channel for computing the average and standard deviation, then adding a new data point, then updating the average and standard deviation. In certain embodiments, a new point is always accepted (i.e., no outliers are rejected). Then the pedestal high and low levels are updated to plus and minus 1.28 times the standard deviation, respectively. It is noted that 1.28 is an exemplary value, and other values may be used. It is also noted that the average is not included in the calculation of the high and low levels since the levels deal with an adjusted spectral density.

Next, the breath detection algorithm switches from a noise-processing state to a breath-processing state, if necessary (step 417). In certain embodiments, only two states exist: breath-processing state and noise-processing state. In certain embodiments, the algorithm may already be in the breath-processing state, in which case no switch is necessary. The only alternate state is the noise-processing state. The algorithm switches its state to a breath-processing state according to the logic described in steps 409-415.

The next steps relate to processing of a breath signal. In step 418, the one-sided power spectral density obtained in step 408 is now used. A spectrum pedestal estimator is also used. The spectrum pedestal is different from the auxiliary pedestal employed in steps 409-412.

Next, the pedestal average is subtracted from the one-sided power spectral density (step 419). This produces a pedestal-adjusted spectral density.

Next, the breath signature is calculated (step 420). In order to calculate the breath signature, the pedestal-adjusted spectral density is examined over a frequency range (step 420.1). In advantageous embodiments, the frequency range is 200 Hz to 800 Hz. Then, the channel values are averaged within the frequency range (step 420.2). Only those values that are, for example, 1.0 dB beyond the pedestal low and high enter the averaging process. Other values are treated as zero. Then a real-time low-pass filter is applied to the signature (step 420.3). In advantageous embodiments, the cut-off frequency of the low-pass filter is set to 0.375 Hz. It is noted that the breath signature has the units of dB, which is inherited from the pedestal-adjusted spectral density.

Next, the reduced total power is determined (step 421). The reduced total power is determined by integrating the pedestal-adjusted spectral density to obtain a total power, then dividing the total power by the integration range. In advantageous embodiments, the integration range is equal to 2400 Hz.

Next, two or more consecutive breaths that are less than a specified time interval apart are consolidated to one breath (step 422). The noise data between the consolidated breaths is not included in the pedestal calculation of this section. In certain embodiments, the specified time interval is equal to 0.0 second, thus no breaths are consolidated.

Next, in certain embodiments, short breaths are discarded (step 423). A breath must be longer than a threshold value, or it is considered a short breath. The threshold value may be set accordingly. In certain embodiments, the threshold is 0.0 second. Thus, no breaths are short breaths.

Next, in order to measure the strength of a breath signal, an average signature is determined (step 424). The average signal is determined by integrating the signature over the duration of the corresponding breath (i.e., the signature integral), then dividing the signature integral of a breath by its duration in seconds. Note that the signature integral has units of dB*second, and the average signature has units of dB.

Next, in certain embodiments, in addition to computing the average signature, the method may find the maximum signature value, also called the "peak signature", during the course of a breath (step 425). The peak signature value may also serve as an indicator of breath strength. It is noted that steps 424 and 425 may be applied to the reduced total power to obtain the reduced total power integral, the average reduced total power, and the peak reduced total power.

The detection method shown in FIG. 4 includes several parameters that may be fine-tuned to improve results. For example, the resampling rate in step 403 may be modified to other values (e.g., 1800 Hz, 2000 Hz, 2200 Hz, etc.). The radius of the Lanczos filter may be modified to 2.0 or 2.5 times the sample window, for example. The overlap of data windows may be modified to other values (e.g., 88%, 92%, etc.). The alpha value of the Kaiser window may be changed to 7 or 8, for example. Other values may be used to improve the detection method.

Figure 5:
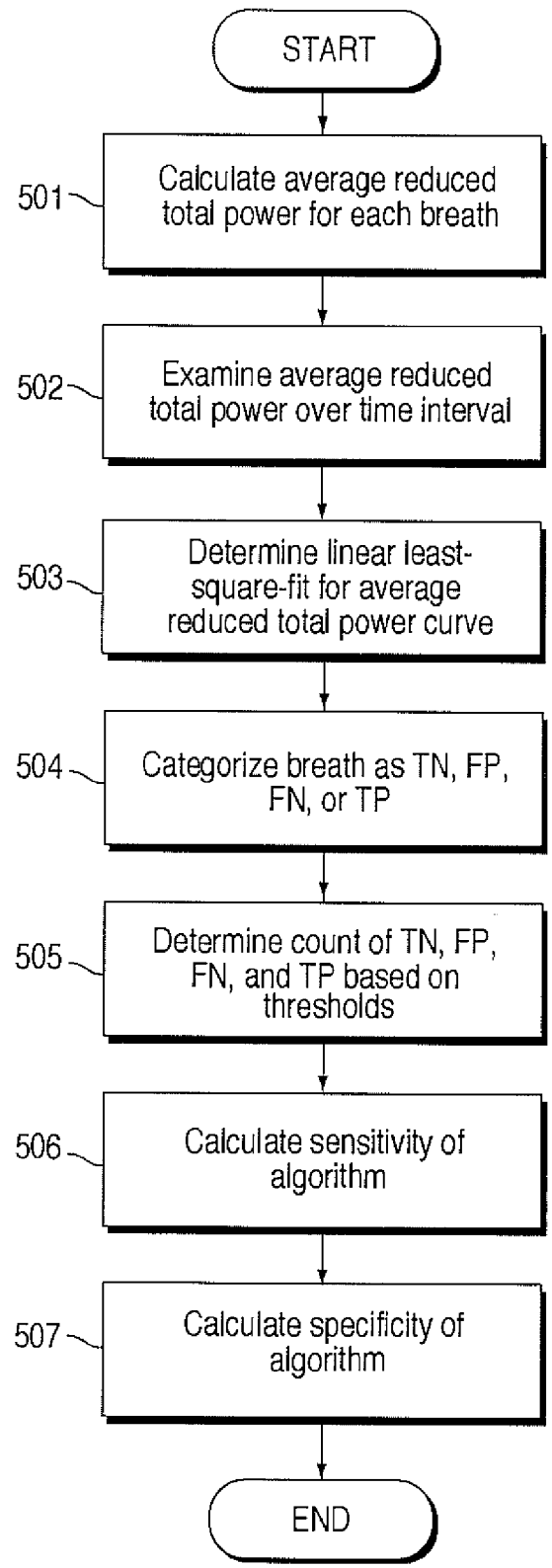
FIG. 5 depicts a method for predicting the onset of an apnea event, according to one embodiment of the present disclosure.

FIG. 5 depicts a method for anticipating the onset of an apnea event, according to one embodiment of the present disclosure. If the anticipation of an apnea event is made sufficiently early, intervention can be made to improve the sleep quality for the sleeping person. In certain embodiments, the method may be implemented as an algorithm or computer program in a data processing system.

First, one or more breaths are detected, and the average reduced total power for each breath is calculated (step 501). In advantageous embodiments, the average reduced total power is calculated according to the method for detecting general events, as described above and shown in FIG. 4.

Next, the average reduced total power of each breath over a particular time interval is examined (step 502). In advantageous embodiments, the time interval may comprise the most recent twenty seconds. Such an interval may span approximately five breaths. In certain embodiments, the length of the time interval may be changed up or down for better results.

Next, a linear least-square-fit is determined for the time vs. the average reduced total power curve (step 503). The resulting curve is used for trending. The slope of the curve from the fit can be negative, positive, or zero. The three cases correspond to the situation where the breath power is decreasing, increasing, or indeterminate, respectively.

Next, the breath is categorized based on the average reduced total power and the slope from the fit (step 504). If the average reduced total power is greater than a threshold value $P_c$, the breath is considered to be negative. If the slope is greater than a threshold value $S_c$, the breath is considered to be negative. If neither the average reduced total power nor the slope is greater than its respective threshold, the breath is considered to be positive. Thus, a breath is considered to be positive if its power is weak (average reduced total power not greater than $P_c$) and if the breath power has been decreasing over a time interval (slope not greater than $S_c$).

In addition to the positive or negative classification of a breath, it is necessary to determine whether a positive breath is actually true, in which case an apnea event follows, or false where no apnea event follows. One approach is to introduce a threshold $\tau_c$ in time-to-event. The time-to-event of a breath is calculated by subtracting the start time of the nearest apnea event occurring after the breath from the start time of the breath, so that the time-to-event is always negative. Since the time-to-event serves to measure the distance of the breath from its nearest apnea event, comparison of the time-to-event with threshold $\tau_c$ determines if an onset indicator is true or false.

Next, using the three thresholds $P_c$, $S_c$, and $\tau_c$, the number of data points for true negatives, false positives, false negatives, and true positives are counted (step 505). The numbers are denoted as TN, FP, FN, and TP, respectively. FIG. 6 depicts this in graphical form. In the graph, the threshold $P_c$ is shown as a horizontal line. Points of data below the line are considered positive, while points of data above the line are considered negative. The threshold $\tau_c$ is shown as a vertical line. The vertical line separates true negatives from false negatives, and false positives from true positives, as shown in the graph.

Next, in step 506, the sensitivity of the apnea-prediction algorithm is calculated via a formula:

$$\text{Sensitivity} = \frac{TP}{TP + FN} \times 100\%$$

Next, in step 507, the specificity of the apnea-prediction algorithm is calculated via a formula:

$$\text{Specificity} = \frac{TN}{TN + FP} \times 100\%$$

Generally, there is a trade-off between sensitivity and specificity. In certain embodiments, high sensitivity (e.g., greater than 90%) may be achieved at the cost of low specificity. For example, in one test, the sensitivity was as high as 94.6% at the cost of low specificity. In another test using different thresholds, the sensitivity decreased to 74.8%, but the specificity increased to 43.1%. In certain embodiments, even higher levels of specificity (e.g., greater than 90%) may be achieved. This may be useful if the sleeping person's breathing is characterized by many hypopnea events.

The method disclosed herein is excellent in the detection of true positive events (sensitivity). In order to improve specificity (i.e., decrease the false positive rate), a specificity improvement algorithm can be used. The specificity improvement algorithm is tuned to the patient and calibrated when he or she is awake and breathing normally. These "normal" breaths are then characterized. After the disclosed method is used and an event is detected, the specificity improvement algorithm is applied. If the breath is determined to be a "normal" breath, the event is cancelled.

Table 1 depicts sensitivity and specificity at various thresholds in the sleep study of a particular patient. The values were obtained using a time-to-event threshold $\tau_c$ of −3.0 min for true/false classification. Although not shown in Table 1, it was observed that the sensitivity and specificity tend to be more responsive to the slope threshold $S_c$ than to the time-to-event threshold $\tau_c$.

TABLE 1

| Average reduced total power threshold (dB) | Slope threshold (dB/sec) | Sensitivity (%) | Specificity (%) |
|---|---|---|---|
| 20.83 | 0.0 | 71.8 | 40.9 |
| 8.33 | 0.0 | 70.6 | 41.4 |
| 4.16 | 0.0 | 66.7 | 43.5 |
| 8.33 | +0.04 | 90.2 | 11.9 |
| 6.25 | +0.04 | 88.7 | 12.6 |

Although the methods disclosed herein have been described with respect to anticipation and prevention of obstructive sleep apnea events, it is noted that these methods may be used and/or adapted for use in the anticipation, detection, and prevention of other sleep disorders (e.g., hypopnea and RERA) and other medical conditions. For example, for asthma, the disclosed methods may be used to detect the narrowing of the airway passages in the lungs, thus providing warning of a dangerous deterioration in respiratory function. For cystic fibrosis, the disclosed methods can be used to detect the occurrence of mucus plugs. For emphysema, the disclosed methods can be used to detect labored breathing suggestive of a severe pulmonary challenge. For prevention of a stroke, after establishment of baseline values, the disclosed methods can be used to detect changes in spectral power suggestive that plaque buildups were becoming deranged.

The disclosed methods may also be useful in industrial applications or in any other processes involving fluids, gases or liquids, where the detection of changes in the power spectrum of flow would be suggestive of an anomaly requiring attention.

It may be advantageous to set forth definitions of certain words and phrases used throughout this patent document. The term "couple" and its derivatives refer to any direct or indirect communication between two or more elements, whether or not those elements are in physical contact with one another. The terms "transmit," "receive," and "communicate," as well as derivatives thereof, encompass both direct and indirect communication. The terms "include" and "comprise," as well as derivatives thereof, mean inclusion without limitation. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like. The term "controller" means any device, system, or part thereof that controls at least one operation. A controller may be implemented in hardware, firmware, software, or some combination of at least two of the same. The functionality associated with any particular controller may be centralized or distributed, whether locally or remotely.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A method for anticipating an onset of an obstructive sleep apnea (OSA) event, the method comprising:
   receiving, at a processor, signals associated with a plurality of breaths;
   determining, at the processor, an average reduced total power of each of the breaths;
   determining, at the processor, a linear least-square-fit of a power curve associated with the average reduced total power of the breaths; and
   based on the average reduced total power and the linear least-square-fit, categorizing, at the processor, each breath as one of: a positive breath and a negative breath, wherein the processor is in communication with at least one microphone.

2. The method as set forth in claim 1, wherein the average reduced total power is determined over a predetermined time interval.

3. The method as set forth in claim 1, wherein the signals associated with the plurality of breaths are received from at least one microphone adjacent a neck of a sleeping person.

4. The method as set forth in claim 1, wherein determining the average reduced total power comprises:
   determining a pedestal-adjusted spectral density;
   integrating the pedestal-adjusted spectral density over an integration range to obtain a total power; and
   dividing the total power by the integration range.

5. A system for anticipating an onset of an obstructive sleep apnea (OSA) event, the system comprising:
   at least one microphone; and
   a processor in communication with the at least one microphone, the processor configured to:
      receive signals associated with a plurality of breaths;
      determine an average reduced total power of each of the breaths;
      determine a linear least-square-fit of a power curve associated with the average reduced total power of the breaths; and
      based on the average reduced total power and the linear least-square-fit, categorize each breath as one of: a positive breath and a negative breath.

6. The system as set forth in claim 5, wherein the average reduced total power is determined over a predetermined time interval.

7. The system as set forth in claim 5, wherein the signals associated with the plurality of breaths are received from at least one microphone adjacent a neck of a sleeping person.

8. The system as set forth in claim 5, wherein the processor is further configured to:
   determine a pedestal-adjusted spectral density;
   integrate the pedestal-adjusted spectral density over an integration range to obtain a total power; and
   divide the total power by the integration range.

9. The method as set forth in claim 1, wherein each breath is categorized as positive when the power of the breath is less than a threshold value and the power of the breath in comparison to previous breaths indicates a decrease in breath power over a time interval.

10. The method as set forth in claim 1, further comprising:
    determining a time-to-event for each breath based on a time interval between the each breath and a start time of a corresponding nearest apnea event; and
    based on the time-to-event for the each breath, categorizing the each breath as one of: a true positive breath, a false positive breath, a true negative breath, and a false negative breath.

11. The method as set forth in claim 10, wherein a breath is categorized as a false negative or a true positive when the time-to-event for the breath is greater than a threshold value, and the breath is categorized a true negative or a false positive when the time-to-event for the breath is less than the threshold value.

12. The method as set forth in claim 1, wherein the power curve is determined for the average reduced total power of the breaths over an interval of time.

13. A method for anticipating an onset of an obstructive sleep apnea (OSA) event, the method comprising:
    receiving, at a processor, signals from at least one microphone communicatively coupled to the processor, the signals associated with a plurality of breaths;
    determining, at the processor, an average reduced total power of each of the breaths;
    determining, at the processor, a linear least-square-fit of a power curve associated with the average reduced total power of the breaths; and
    based on the average reduced total power and the linear least-square-fit, categorizing, at the processor, each breath as one of: a positive breath and a negative breath.

14. The method as set forth in claim 13, wherein the average reduced total power is determined over a predetermined time interval.

15. The method as set forth in claim 13, wherein at least one microphone is adjacent to a neck of a sleeping person.

16. The method as set forth in claim 13, wherein determining the average reduced total power comprises:
   determining a pedestal-adjusted spectral density;
   integrating the pedestal-adjusted spectral density over an integration range to obtain a total power; and
   dividing the total power by the integration range.

17. The method as set forth in claim 13, wherein each breath is categorized as positive when the power of the breath is less than a threshold value and the power of the breath in comparison to previous breaths indicates a decrease in breath power over a time interval.

18. The method as set forth in claim 13, further comprising:
   determining a time-to-event for each breath based on a time interval between the each breath and a start time of a corresponding nearest apnea event; and
   based on the time-to-event for the each breath, categorizing the each breath as one of: a true positive breath, a false positive breath, a true negative breath, and a false negative breath.

19. The method as set forth in claim 18, wherein a breath is categorized as a false negative or a true positive when the time-to-event for the breath is greater than a threshold value, and the breath is categorized a true negative or a false positive when the time-to-event for the breath is less than the threshold value.

20. The method as set forth in claim 13, wherein the power curve is determined for the average reduced total power of the breaths over an interval of time.

* * * * *